United States Patent [19]

Poulos et al.

[11] Patent Number: 5,466,695
[45] Date of Patent: Nov. 14, 1995

[54] METHOD FOR STIMULATING HAIR GROWTH WITH CATIONIC DERIVATIVE OF MINOXIDIL USING THERAPEUTIC IONTOPHORESIS

[75] Inventors: Charles W. Poulos, Claremore; George M. Brenner, Jenks; Loyd V. Allen, Jr., Midwest City; Vilas A. Prabhu; Pedro L. Huerta, Jr., both of Weatherford, all of Okla.

[73] Assignee: Tulsa Forte Pharmacy Enterprises, Inc., Tulsa, Okla.

[21] Appl. No.: 272,880

[22] Filed: Jul. 11, 1994

Related U.S. Application Data

[63] Continuation of Ser. No. 15,396, Feb. 9, 1993, abandoned.

[51] Int. Cl.$^6$ .................................................. A61K 31/505
[52] U.S. Cl. ........................................................ 514/275
[58] Field of Search ............................................ 514/275

[56] References Cited

U.S. PATENT DOCUMENTS

| | | | |
|---|---|---|---|
| 3,991,755 | 11/1976 | Vernon et al. | 128/172.1 |
| 4,139,619 | 2/1979 | Chidsey, III | 424/45 |
| 4,141,359 | 2/1979 | Jacobsen et al. | 128/172.1 |
| 4,474,570 | 10/1984 | Ariura et al. | 604/20 |
| 4,596,812 | 6/1986 | Chidsey, III et al. | 514/256 |
| 4,640,689 | 2/1987 | Sibalis | 604/20 |
| 4,722,726 | 2/1988 | Sanderson et al. | 604/20 |
| 4,752,285 | 6/1988 | Petelenz et al. | 604/20 |
| 4,820,512 | 4/1989 | Grollier | 424/70 |
| 4,828,837 | 5/1989 | Uster et al. | 424/450 |
| 4,871,839 | 10/1989 | Gibson | 536/55.1 |
| 4,968,685 | 11/1990 | Grollier | 514/256 |
| 4,970,063 | 11/1990 | Lang et al. | 424/47 |
| 4,979,938 | 12/1990 | Stephen et al. | 604/20 |
| 4,997,418 | 3/1991 | DeMartini | 604/20 |
| 5,006,332 | 4/1991 | Grollier | 424/70 |
| 5,030,442 | 7/1991 | Uster et al. | 424/45 |
| 5,034,387 | 7/1991 | Maignan et al. | 514/235.8 |
| 5,195,953 | 3/1993 | DeMartini | 604/20 |

FOREIGN PATENT DOCUMENTS

| | | |
|---|---|---|
| 0273202 | 7/1988 | European Pat. Off. . |
| 3537211 | 4/1986 | Germany . |

OTHER PUBLICATIONS

Masaki, *Chemical Abstract*, vol. 103(20), No. 165920h, 1985.

*Primary Examiner*—Raymond Henley, III
*Assistant Examiner*—William R. A. Jarvis
*Attorney, Agent, or Firm*—Head & Johnson

[57] ABSTRACT

This invention relates to a method of applying a cationic derivative of Minoxidil which is transported by means of iontophoresis to hair follicles where the cationic derivatives promote hair growth. Each of the cationic derivatives of Minoxidil are synthesized by reacting the Minoxidil parent compound with an organic or an inorganic acid to form the cationic derivative.

15 Claims, No Drawings

METHOD FOR STIMULATING HAIR GROWTH WITH CATIONIC DERIVATIVE OF MINOXIDIL USING THERAPEUTIC IONTOPHORESIS

This is a continuation of application Ser. No. 08/015,396 filed on Feb. 9, 1993, now abandoned.

BACKGROUND OF THE DISCLOSURE

1. Field of the Invention

This invention relates to an improved method of application of Minoxidil to stimulate hair growth by means of iontophoretic transport to the hair follicle after converting Minoxidil to an ionic form.

2. Background of the Invention

The patent literature is replete with compositions and processes for stimulating mammalian hair growth and/or keratin formation. Of these, Minoxidil (6-piperidino-2,4-diaminopyrimidine-3-oxide) is a drug which has been found to be useful in promoting hair growth. Minoxidil is normally applied as an active ingredient topically to the area where hair growth is desired. U.S. Pat. No. 4,970,063 describes and defines compositions and methods using what is defined as "Minoxidil," said patent being incorporated herein by reference. Other U.S.A. patents which teach the use of Minoxidil for hair growth are U.S. Pat. Nos. 3,461,461; 3,910,928; 4,139,619; and 4,596,812. It is believed that Minoxidil promotes hair growth after diffusion to the hair follicles. The precise site and mechanism of action have not as yet been elucidated.

Although Minoxidil is effective in promoting hair growth after it reaches the hair follicle, the clinical efficacy of topical application is limited by low water solubility and by the fact that the outer layers of skin are an effective barrier to penetration of polar molecules such as Minoxidil.

The technique of iontophoresis employs a small electric current to transport ionic drug compounds into the skin or other tissue. Iontophoresis is believed to increase drug entry through so-called "shunt pathways" provided by hair follicles and sweat glands. Since hair follicles are a major pathway for iontophoretic drug delivery, iontophoresis is potentially the ideal method of administering Minoxidil to the hair follicles.

Water is the preferred solvent for use in iontophoresis. Minoxidil itself has a low solubility in water and, because it has no net ionic charge, does not migrate in an iontophoretic field. In fact, due to the dipolar nature of Minoxidil, there is some evidence that the iontophoretic field inhibits even the passive migration by electro-osmosis often observed with non-charged compounds in electric fields.

Thus, although Minoxidil is effective in promoting hair growth after it reaches the hair follicles, presently there has been no therapeutic delivery system that utilized a transport mechanism other than passive diffusion in its attempt to deliver Minoxidil across the skin's membrane barrier to the hair follicle.

SUMMARY OF THE INVENTION

The present invention is directed to the application of ionic derivatives or salts of Minoxidil which can effectively be transported via iontophoresis to hair follicles where they promote hair growth.

Specifically, the invention is directed to the cationic derivatives of Minoxidil, such as taught in the aforesaid U.S. Pat. No. 4,970,063, which are purified and then applied in an electric conductive solution, usually aqueous, to the area where hair growth is desired and transported to the hair follicles by means of iontophoresis.

DETAILED DESCRIPTION OF THE PREFERRED EMBODIMENT

The term "Minoxidil" as used herein refers to the compound 6-(1-piperidinyl)-2,4-pyrimidinediamine 3-oxide (the uninverted name used by Chemical Abstracts Service during the ninth and/or subsequent Collective Index Periods and having the Chemical Abstracts Registry Number [38304-91-5]). The Merck Index, Eleventh Edition (published by Merck & Co., Inc., Rathway, N.J., U.S.A., 1989) lists a number of other names, including 6-piperidino-2,4-diaminopyrimidine 3-oxide and 6-amino-1,2-dihydro-1-hydroxy-2-imino-4-piperidinopyrimidine, one of the tautomers of Minoxodil. Reference is also made to U.S. Pat. Nos. 4,970,063 and 3,461,461. Ionic specifically cationic derivatives of Minoxidil are formed according to a preferred embodiment of the present invention by means such as set forth in the following general procedure.

GENERAL PROCEDURE FOR CREATING IONIC DERIVATIVES OF MINOXIDIL

A solution of 4.2 g (0.02 mole) of Minoxidil (6-piperidino-2,4-diaminopyrimidine-3-oxide) in 100 ml of 95% alcohol at about 70° C. is placed in a 500 ml three-necked flask equipped with a reflux condenser, stirrer and a dropping funnel. The stoichiometric amount of an organic acid (0.01 mole of d-tartaric acid or 0.02 mole of one of the other acids listed below) dissolved in 100 ml of 95% ethanol at a temperature of about 70° C. was placed in the dropping funnel and added to the stirred Minoxidil solution in a dropwise fashion over a period of about one hour. Upon completion of the addition, the reaction mixture is stirred, for from 16 to 24 hours, while being maintained at a temperature of about 70° C. Any significant amount of solid present is removed by filtration. The remaining solution is transferred to a 500 ml one-necked flask and concentrated to about 50 ml under reduced pressure using a Roto Vac device. The precipitates formed are collected by vacuum filtration and purified by recrystallization from absolute alcohol.

Seven prototype salts or cationic derivatives were prepared using the general procedure. The salt obtained from the reaction with 5-nitro-2-furoic acid was bright yellow in color; all other compounds were white solids. The salts were characterized by their melting points, elemental analyses, infrared spectra, proton NMR spectra and carbon 13 NMR spectra. The percentage yields, melting points and elemental analyses are summarized in Table 1.

TABLE 1

| ORGANIC ACID REACTANT | MOLECULAR FORMULA OF PRODUCT | % YIELD | MELTING POINT, °C. | ELEMENTAL ANALYSIS | % C | % H | % N |
|---|---|---|---|---|---|---|---|
| [R-(R*,R*)]-2,3-dihydroxy-butanedioc acid (d-tartaric acid) | $C_{22}H_{36}N_{10}O_8$ | 87% | 212–214 | Theory | 47.14 | 6.47 | 24.99 |
| | | | | Found | 46.48 | 6.19 | 24.46 |
| 2,4,6(1H,3H,5H)-pyrimidinetrione (barbituric acid) | $C_{13}H_{19}N_7O_4$ | 86% | 198–200 | Theory | 46.29 | 5.68 | 29.06 |
| | | | | Found | 45.05 | 5.77 | 28.16 |
| 3,4-dihydroxy-benzoic acid (protocatechuic acid) | $C_{16}H_{21}N_5O_5$ | 89% | 212–214 | Theory | 52.89 | 5.83 | 19.27 |
| | | | | Found | 52.49 | 5.96 | 22.37 |
| 2,3,4-trihydroxy-benzoic acid | $C_{16}H_{21}N_5O_6$ | 62% | 226–228 | Theory | 50.66 | 5.58 | 18.46 |
| | | | | Found | 50.22 | 5.57 | 20.13 |
| 3,4,5-trihydroxy-benzoic acid (gallic acid) | $C_{16}H_{21}N_5O_6$ | 85% | 211–212 | Theory | 50.66 | 5.58 | 18.46 |
| | | | | Found | 50.63 | 5.84 | 21.82 |
| 5-nitro-2-furoic acid | $C_{14}H_{18}N_6O_6$ | 55% | 226–228 | Theory | 45.90 | 4.95 | 22.94 |
| | | | | Found | 45.81 | 4.82 | 22.84 |
| 5,5-dimethyl-oxazolidine-2,4-dione (dimethadione) | $C_{14}H_{22}N_6O_4$ | 65% | 165–167 | Theory | 49.70 | 6.55 | 24.84 |
| | | | | Found | 50.21 | 6.68 | 26.16 |

Equations for the reactions of Minoxidil with the seven organic acids listed in Table 1 are listed below.

Equations for the reactions of Minoxidil with various acids

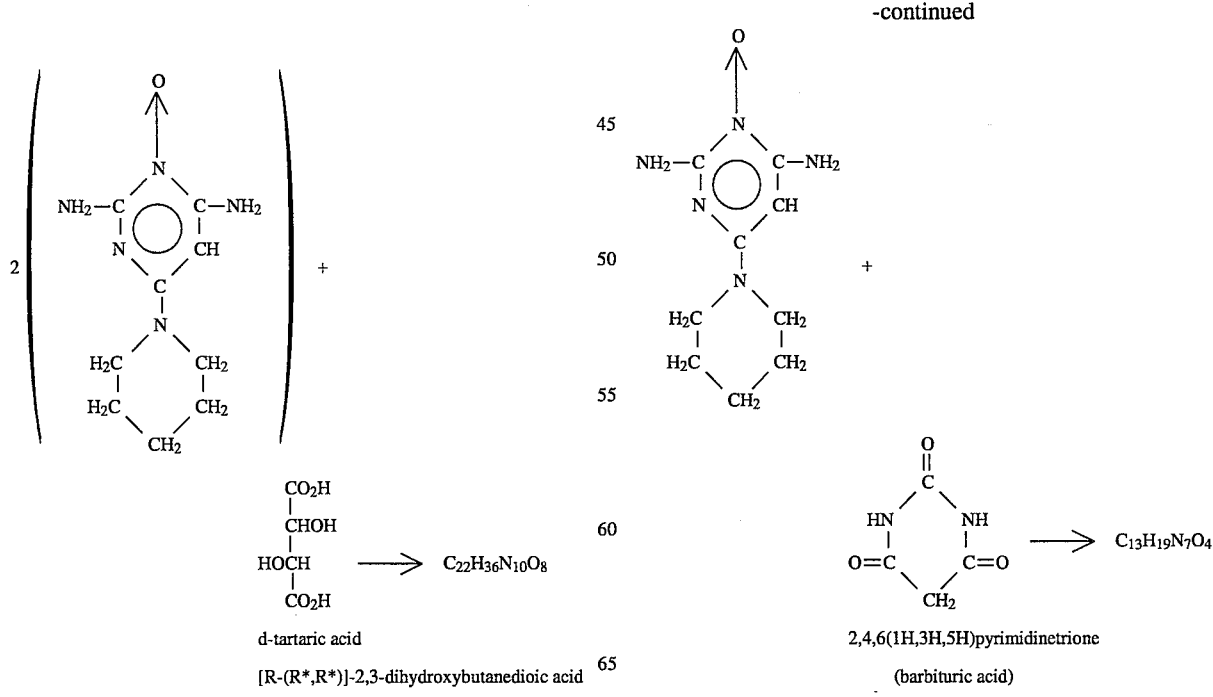

-continued
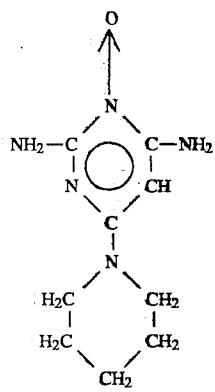
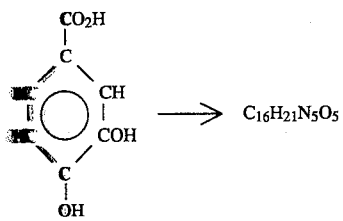 → $C_{16}H_{21}N_5O_5$
3,4-dihydroxybenzoic acid
(protocatechuic acid)
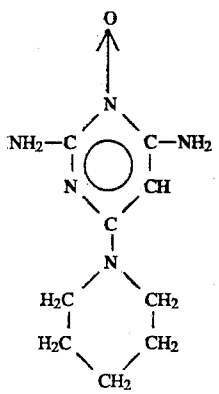
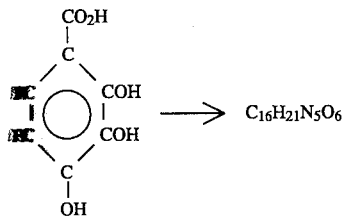 → $C_{16}H_{21}N_5O_6$
2,3,4-trihydroxybenzoic acid
-continued
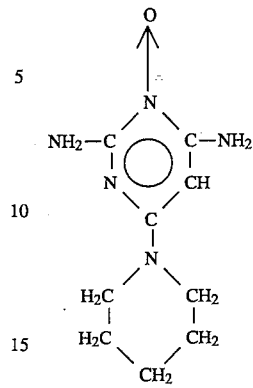
+
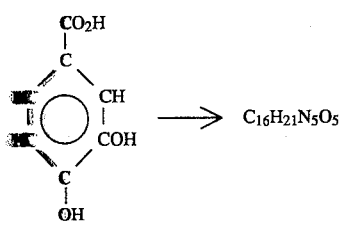 → $C_{16}H_{21}N_5O_6$
3,4,5-trihydroxybenzoic acid
(gallic acid)
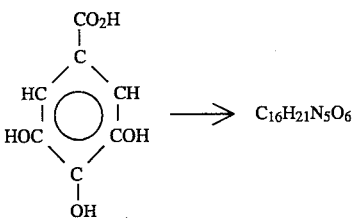
+
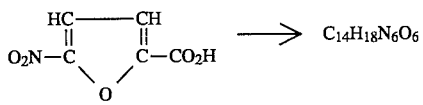 → $C_{14}H_{18}N_6O_6$
5-nitro-2-furoic acid
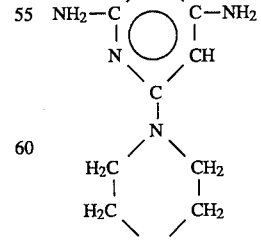
+

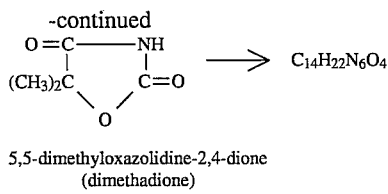

5,5-dimethyloxazolidine-2,4-dione
(dimethadione)

The cationic derivatives of Minoxidil are not limited to those produced by the seven acids which are listed but may be produced with other organic and inorganic acids.

measured by ultraviolet spectrophotometry. Data was also obtained under passive conditions without any electric current. The results of 4 to 8 separate experiments with each Minoxidil ionic derivative were used to calculate the average flux for passive and active iontophoretic conditions and these data are shown in Table 2 below. Iontophoresis significantly enhanced the skin permeation of the Minoxidil ionic derivatives. The Minoxidil tartrate derivative of those tested showed significant improvement in iontophoretic mobility across the skin. These results demonstrate that iontophoresis can be used to enhance the delivery of Minoxidil to the skin.

TABLE 2

Active (Iontophoretic) and Passive Flux (ug/cm$^2$/h) of Minoxidil Ionic Derivates[1]

| MINOXIDIL IONIC DERIVATES[2] | 5–30 MINUTES | 30–90 MINUTES | 5–90 MINUTES |
|---|---|---|---|
| Dimethadione 0.1% | | | |
| ACTIVE | 68.6 ± 10.3 | 136.0 ± 19.8 | 95.8 ± 13.3 |
| PASSIVE | 25.7 ± 5.5 | 25.8 ± 2.4 | 17.2 ± 1.6 |
| Dimethadione 0.2% | | | |
| ACTIVE | 74.0 ± 15.3 | 146.6 ± 9.9 | 97.7 ± 6.6 |
| PASSIVE | 34.9 ± 5.8 | 29.2 ± 1.7 | 19.5 ± 1.2 |
| Tartrate 0.1% | | | |
| ACTIVE | 65.4 ± 19.4 | 189.7 ± 36.2 | 144.6 ± 23.0 |
| PASSIVE | 59.2 ± 17.6 | 25.6 ± 6.2 | 29.6 ± 6.6 |
| Tartrate 0.2% | | | |
| ACTIVE | 74.3 ± 21.8 | 180.4 ± 26.7 | 140.9 ± 22.7 |
| PASSIVE | 23.3 ± 4.7 | 20.6 ± 6.8 | 20.2 ± 5.8 |
| Trihydroxybenzoate 0.1% | | | |
| ACTIVE | 37.2 ± 5.8 | 62.4 ± 9.9 | 59.7 ± 7.8 |
| PASSIVE | 24.7 ± 4.3 | 24.5 ± 3.4 | 21.9 ± 3.6 |
| Trihydroxybenzoate 0.2% | | | |
| ACTIVE | 53.2 ± 5.6 | 173.9 ± 29.0 | 115.9 ± 19.4 |
| PASSIVE | 4.3 ± 1.9 | 6.0 ± 1.8 | 4.0 ± 1.2 |

[1]Values are the mean and standard error of 4 to 8 separate studies.
[2]The terminology for the derivatives is expressed as the common name for the acid used and the concentration is expressed as percentage of Minoxidil base.

IONTOPHORETIC TRANSPORT OF CATIONIC DERIVATIVES OF MINOXIDIL

The transdermal iontophoresis of cationic derivatives of Minoxidil was demonstrated in laboratory experiments utilizing fresh, full-thickness mouse skin with clipped hair, which has been reported to be an excellent model for studying the drug permeability of human skin. Iontophoresis was conducted with side-by-side diffusion cells obtained from the Crown Glass Co. A piece of mouse skin was clamped between the two half-cells, and the donor cell was filled with an aqueous solution of one of the ionic derivatives of Minoxidil. The receiver cell was filled with 0.05 molar sodium chloride solution. An electric current was applied across the two half-cells using silver/silver chloride electrodes inserted into both cells through teflon plugs. The donor cell electrode was always the anode (positive pole +) except where otherwise noted. An electric stimulator was used to apply a 0.8 milliamp, current to a diffusion area of 0.64 cm$^2$ for periods of up to 90 minutes, and the iontophoretic mobility of the ionic derivatives of Minoxidil was determined by sampling the receiver cell compartment at various times throughout the study. The concentration of cationic derivatives of Minoxidil in the receiver cell was In practice, one method of practicing the invention is to mix the cationic derivative salt of Minoxidil as a distilled water solution in proportion of 0.1 mg/ml to a saturated solution. An iontophoretic device such as manufactured and sold by General Medical Co. under the registered mark LECTRO PATCH would be used. Both treatment pads are saturated with the Minoxidil salt solution. The saturated treatment pads are placed on the skin where enhanced growth is desired. This particular device will only accept up to 1 milliamp (mA) of current. Other iontophoretic devices, such as New Life Litronic Stimulator manufactured by Mid-western Electronics Inc. Model No. 0880 can deliver up to 0.5 mA per cm$^2$ can also be used. The tolerance of an individual patient determines time and milliamp limits above 0.5 mA per cm$^2$.

While the invention has been described with a certain degree of particularity, it is manifest that many changes may be made in the details of construction and the arrangement of components without departing from the spirit and scope of this disclosure. It is understood that the invention is not limited to the embodiment set forth herein for purposes of exemplification, but is to be limited only by the scope of the attached claimed or claims, including the full range of equivalency to which each element thereof is entitled.

What is claimed is:

1. A pharmaceutically acceptable composition useful in promoting mammalian hair growth when applied using iontophoresis comprising a cationic derivative of Minoxidil in solution, wherein the cationic derivative of Minoxidil is formed by mixing solutions of Minoxidil with an organic acid selected from the group consisting of:

[R-(R*,R*)]-2,3-dihydroxybutanedioic acid (also known as d-tartaric acid);
2,4,6(1H,3H,5H)-pyrimidinetrione (also known as barbituric acid);
3,4-dihydroxybenzoic acid (also known as protocatechuic acid);
2,3,4-trihydroxybenzoic acid;
3,4,5-trihydroxybenzoic acid (also known as gallic acid);
5-nitro-2-furoic acid; and
5,5-dimethyloxazolidine-2-4-dione (also known as dimethadione).

2. The composition according to claim 1 wherein the solutions are mixed at 70° C.

3. The composition according to claim 1 wherein the solutions are mixed and stirred for up to 24 hours.

4. A pharmaceutically effective topical composition for promoting hair growth in humans using iontophoresis, said composition comprising a pharmaceutical solution of Minoxidil tartrate possessing a superior water solubility.

5. A pharmaceutically acceptable composition useful in promoting mammalian hair growth when applied using iontophoresis comprising a cationic derivative of Minoxidil in solution, wherein the cationic derivative of Minoxidil is derived by mixing solutions of Minoxidil with (R-(R*,R*))-2,3-dihydroxybutanedioic acid (also known as d-tartaric acid).

6. A method of promoting hair growth on skin of a human or animal comprising the steps of applying a pharmaceutically effective amount of a cationic derivative of Minoxidil to said skin, said cationic derivative of Minoxidil formed by mixing solutions of Minoxidil with an organic acid selected from the group consisting of;
(R-(R*,R*))-2,3-dihydroxybutanedioic acid (also known as d-tartaric acid);
2,4,6(1H,3H,5H)-pyrimidinetrione (also known as barbituric acid);
3,4-dihydroxybenzoic acid (also known as protocatechuic acid);
2,3,4-trihydroxybenzoic acid;
3,4,5-trihydroxybenzoic acid (also known as gallic acid);
5-nitro-2-furoic acid;
5,5-dimethyloxazolidine-2-4-dione (also known as dimethadione); and
applying electric current to the skin sufficient to create iontophoresis to transport said cationic derivative of Minoxidil to the hair follicles.

7. The method of claim 6 wherein said cationic derivative of Minoxidil is produced by the steps of:
a) mixing a solution of Minoxidil with a solution of said organic acid at an elevated temperature for a period of time sufficient to form a precipitate;
b) collecting and purifying the precipitate so the precipitate can be used in iontophoresis.

8. The method according to claim 7 wherein the two solutions are mixed at a temperature substantially within the range of 60° C. to 80° C., and stirred for up to 24 hours.

9. A method of promoting mammalian hair growth comprising the steps of applying to a treatment area a cationic derivative of Minoxidil in pharmaceutically effective solutions, said cationic derivative of Minoxidil formed by mixing solutions of Minoxidil with an organic acid selected from the group consisting of:
(R-(R*,R*))-2,3-dihydroxybutanedioic acid (also known as d-tartaric acid);
2,4,6(1H,3H,5H)-pyrimidinetrione (also known as barbituric acid);
3,4-dihydroxybenzoic acid (also known as protocatechuic acid);
2,3,4-trihydroxybenzoic acid;
3,4,5-trihydroxybenzoic acid (also known as gallic acid);
5-nitro-2-furoic acid; and
5,5-dimethyloxazolidine-2-4-dione (also known as dimethadione); and
applying said solution to the treatment area electrical current to create iontophoresis and thereby transport Minoxidil molecules to hair follicles.

10. The method of claim 9 wherein the amount of current is within the range including and between 0.08 and 1.25 mAmp per square centimeter of said treatment area.

11. A method of promoting hair growth on an area of skin of a human or animal to be treated, comprising the steps of applying a pharmaceutically effective amount of a cationic derivative of Minoxidil to a positive donor electrode of an iontophoresis apparatus having a negative receiver electrode, said cationic derivative of Minoxidil formed by mixing solutions of Minoxidil with an organic acid selected from the group consisting of:
(R-(R*,R*))-2,3-dihydroxybutanedioic acid (also known as d-tartaric acid);
2,4,6(1H,3H,5H)-pyrimidinetrione (also known as barbituric acid);
3,4-dihydroxybenzoic acid (also known as protocatechuic acid);
2,3,4-trihydroxybenzoic acid;
3,4,5-trihydroxybenzoic acid (also known as gallic acid);
5-nitro-2-furoic acid; and
5,5-dimethyloxazolidine-2-4-dione (also known as dimethadione);
and applying said electrodes and electric current to the area to be treated.

12. A method according to claim 11 wherein said receiver electrode includes a sodium chloride solution.

13. The method of claim 12 wherein said electric current is applied across said cells in the amount of between 0.08 and 1.25 mA of said treatment area.

14. The method of claim 11 wherein said cationic derivative of Minoxidil is formed from organic d-tartaric acid.

15. A method of promoting mammalian hair growth comprising the steps of applying to a treatment area a cationic derivative of Minoxidil in a pharmaceutically effective solution, said solution formed by mixing a solution of Minoxidil with (R-(R*,R*))-2,3-dihydroxybutanedioic acid (also known as d-tartaric acid); and applying an electrical current to said treatment area to create iontophoresis and thereby transport Minoxidil molecules to hair follicles.

* * * * *